United States Patent
Piaggio et al.

(10) Patent No.: US 10,114,018 B2
(45) Date of Patent: Oct. 30, 2018

(54) IL-2 PEPTIDE DERIVATIVES, AND USES THEREOF FOR THE DIAGNOSIS AND TREATMENT OF AN AUTOIMMUNE DISEASE

(71) Applicants: INSERM (INSTITUT NATIONAL DE LA SANTÉ ET DE LA RECHERCHE MÉDICALE), Paris (FR); INSTITUT CURIE, Paris (FR); UNIVERSITE PARIS DESCARTES, Paris (FR)

(72) Inventors: Eliane Piaggio, Paris (FR); Louis Perol, Paris (FR)

(*) Notice: Subject to any disclaimer, the term of this patent is extended or adjusted under 35 U.S.C. 154(b) by 6 days.

(21) Appl. No.: 15/305,548

(22) PCT Filed: Apr. 21, 2015

(86) PCT No.: PCT/EP2015/058588
§ 371 (c)(1),
(2) Date: Oct. 20, 2016

(87) PCT Pub. No.: WO2015/162124
PCT Pub. Date: Oct. 29, 2015

(65) Prior Publication Data
US 2017/0045512 A1    Feb. 16, 2017

(30) Foreign Application Priority Data
Apr. 22, 2014 (EP) .................................... 14305595

(51) Int. Cl.
| | |
|---|---|
| *A61K 38/00* | (2006.01) |
| *A61K 38/10* | (2006.01) |
| *G01N 33/564* | (2006.01) |
| *C07K 14/47* | (2006.01) |
| *G01N 33/00* | (2006.01) |
| *C07K 14/55* | (2006.01) |
| *C07K 16/24* | (2006.01) |

(52) U.S. Cl.
CPC ....... *G01N 33/564* (2013.01); *C07K 14/4713* (2013.01); *C07K 14/55* (2013.01); *C07K 16/246* (2013.01); *G01N 33/00* (2013.01); *A61K 38/00* (2013.01); *C07K 2317/14* (2013.01); *G01N 2333/55* (2013.01); *G01N 2800/24* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,083,503 A * | 7/2000 | Lenardo ............. | A61K 38/2013 424/184.1 |
| 6,168,785 B1 | 1/2001 | Theze et al. | |
| 2009/0274647 A1* | 11/2009 | Montero Casimiro ...................... | A61K 39/0005 424/85.2 |
| 2012/0077709 A1 | 3/2012 | Ellis et al. | |
| 2014/0004080 A1 | 1/2014 | Klatzmann et al. | |

FOREIGN PATENT DOCUMENTS

| | | | | |
|---|---|---|---|---|
| EP | 0 262 802 | * | 8/1987 | ............. A61K 37/02 |
| EP | 1829893 A1 | | 9/2007 | |
| UA | 27420 U | | 5/2007 | |
| WO | WO 2007/084651 | * | 7/2007 | ............. A61K 38/20 |
| WO | WO 2012/123381 | * | 9/2012 | ............. A61K 38/20 |

OTHER PUBLICATIONS

Grinberg-Bleyer et al.(2010. J. Exp Med. 207:1871-1878.*
Hartemann et al. 2013. Lancet. Diabetes and Endocrinology 1:295-305.*
J: "Product Data Sheet LEAF(TM) Purified anti-human IL-2", Jan. 1, 2014, XP055146546.
"Product Data Sheet Purified anti-mouse IL-2", Immunol. Rev. J. Immunol. Meth. Abrams J. Curr. Prot. Immunol. Curr. Prot. Immunol. J. Virol. Karulin A J. Immunol. Curr. Prot. Immunol, Nov. 30, 2012, XP055146540.
Long S Alice et al: "IL-12 therapy in type 1 diabetes: Trials and trip", Clinical Immunology, vol. 149, No. 3, Feb. 22, 2013, pp. 324-331.
Nicholas Holdgate et al: "Recent advances in primary Sjogren's syndrome [version 1; referees: 3 approved]", F1000 Research, pp. 1-10, Jun. 17, 2016.
Jens Humrich et al: "Low-Dose IL-2 Therapy in Refractory SLE: Results from Single Center PHase I/IIa Clinical Trial", 2016 ACR/ARHP Annual Meeting, Oct. 19, 2016.
Miao Miao et al: "Low Dose IL-2 Therapy Can Restore the Balance of Th17 and Treg Cells in Refractory Patients with Sjogren's Syndrome", 2016 ACR/ARHP Annual Meeting, Sep. 28, 2016.

* cited by examiner

*Primary Examiner* — Shulamith H Shafer
(74) *Attorney, Agent, or Firm* — W&C IP

(57) ABSTRACT

An in vitro method for determining whether a patient has, or is at risk of having or developing an autoimmune disease or for assessing the severity or predicting the outcome of an autoimmune disease, comprising a step of detecting or quantifying in a biological sample obtained from said patient an immune anti-IL2 response, peptides specifically recognized by anti-IL2 antibodies or IL-2-specific T cells of T1D, systemic lupus erythematosus, rheumatoid arthritis, Sjögren's syndrome and autoimmune polymyositis patients, and pharmaceutical compositions.

4 Claims, 8 Drawing Sheets

Specification includes a Sequence Listing.

SEQUENCE LISTING

<160> NUMBER OF SEQ ID NOS: 37

<210> SEQ ID NO 1
<211> LENGTH: 15
<212> TYPE: PRT
<213> ORGANISM: Artificial Sequence
<220> FEATURE:
<223> OTHER INFORMATION: Synthetic fragment

<400> SEQUENCE: 1

Leu Thr Arg Met Leu Thr Phe Lys Phe Tyr Met Pro Lys Lys Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic fragment

<400> SEQUENCE: 2

Glu Phe Leu Asn Arg Trp Ile Thr Phe Ser Gln Ser Ile Ile Ser
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic fragment

<400> SEQUENCE: 3

Met Tyr Arg Met Gln Leu Leu Ser Cys Ile Ala Leu Ser Leu Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic fragment

<400> SEQUENCE: 4

Leu Leu Ser Cys Ile Ala Leu Ser Leu Ala Leu Val Thr Asn Ser
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic fragment

<400> SEQUENCE: 5

Ala Leu Ser Leu Ala Leu Val Thr Asn Ser Ala Pro Thr Ser Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic fragment

<400> SEQUENCE: 6

Leu Val Thr Asn Ser Ala Pro Thr Ser Ser Ser Thr Lys Lys Thr
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic fragment

<400> SEQUENCE: 7

Ala Pro Thr Ser Ser Ser Thr Lys Lys Thr Gln Leu Gln Leu Glu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic fragment

<400> SEQUENCE: 8

Met Pro Thr Ser Ser Ser Thr Lys Lys Thr Gln Leu Gln Leu Glu
1               5                   10                  15

```
<210> SEQ ID NO 9
<211> LENGTH: 15
<212> TYPE: PRT
<213> ORGANISM: Artificial Sequence
<220> FEATURE:
<223> OTHER INFORMATION: Synthetic fragment

<400> SEQUENCE: 9

Ser Thr Lys Lys Thr Gln Leu Gln Leu Glu His Leu Leu Leu Asp
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic fragment

<400> SEQUENCE: 10

Gln Leu Gln Leu Glu His Leu Leu Leu Asp Leu Gln Met Ile Leu
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic fragment

<400> SEQUENCE: 11

His Leu Leu Leu Asp Leu Gln Met Ile Leu Asn Gly Ile Asn Asn
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic fragment

<400> SEQUENCE: 12

Leu Gln Met Ile Leu Asn Gly Ile Asn Asn Tyr Lys Asn Pro Lys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic fragment

<400> SEQUENCE: 13

Asn Gly Ile Asn Asn Tyr Lys Asn Pro Lys Leu Thr Arg Met Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic fragment

<400> SEQUENCE: 14

Tyr Lys Asn Pro Lys Leu Thr Arg Met Leu Thr Phe Lys Phe Tyr
1               5                   10                  15
```

<210> SEQ ID NO 15
<211> LENGTH: 15
<212> TYPE: PRT
<213> ORGANISM: Artificial Sequence
<220> FEATURE:
<223> OTHER INFORMATION: Synthetic fragment

<400> SEQUENCE: 15

```
Leu Thr Arg Met Leu Thr Phe Lys Phe Tyr Met Pro Lys Lys Ala
1               5                   10                  15
```

<210> SEQ ID NO 16
<211> LENGTH: 15
<212> TYPE: PRT
<213> ORGANISM: Artificial Sequence
<220> FEATURE:
<223> OTHER INFORMATION: Synthetic fragment

<400> SEQUENCE: 16

```
Thr Phe Lys Phe Tyr Met Pro Lys Lys Ala Thr Glu Leu Lys His
1               5                   10                  15
```

<210> SEQ ID NO 17
<211> LENGTH: 15
<212> TYPE: PRT
<213> ORGANISM: Artificial Sequence
<220> FEATURE:
<223> OTHER INFORMATION: Synthetic fragment

<400> SEQUENCE: 17

```
Met Pro Lys Lys Ala Thr Glu Leu Lys His Leu Gln Cys Leu Glu
1               5                   10                  15
```

<210> SEQ ID NO 18
<211> LENGTH: 15
<212> TYPE: PRT
<213> ORGANISM: Artificial Sequence
<220> FEATURE:
<223> OTHER INFORMATION: Synthetic fragment

<400> SEQUENCE: 18

```
Thr Glu Leu Lys His Leu Gln Cys Leu Glu Glu Glu Leu Lys Pro
1               5                   10                  15
```

<210> SEQ ID NO 19
<211> LENGTH: 15
<212> TYPE: PRT
<213> ORGANISM: Artificial Sequence
<220> FEATURE:
<223> OTHER INFORMATION: Synthetic fragment

<400> SEQUENCE: 19

```
Leu Gln Cys Leu Glu Glu Glu Leu Lys Pro Leu Glu Glu Val Leu
1               5                   10                  15
```

<210> SEQ ID NO 20
<211> LENGTH: 15
<212> TYPE: PRT
<213> ORGANISM: Artificial Sequence
<220> FEATURE:
<223> OTHER INFORMATION: Synthetic fragment

<400> SEQUENCE: 20

```
Glu Glu Leu Lys Pro Leu Glu Glu Val Leu Asn Leu Ala Gln Ser
1               5                   10                  15
```

<210> SEQ ID NO 21

<211> LENGTH: 15
<212> TYPE: PRT
<213> ORGANISM: Artificial Sequence
<220> FEATURE:
<223> OTHER INFORMATION: Synthetic fragment

<400> SEQUENCE: 21

Leu Glu Glu Val Leu Asn Leu Ala Gln Ser Lys Asn Phe His Leu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic fragment

<400> SEQUENCE: 22

Asn Leu Ala Gln Ser Lys Asn Phe His Leu Arg Pro Arg Asp Leu
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic fragment

<400> SEQUENCE: 23

Lys Asn Phe His Leu Arg Pro Arg Asp Leu Ile Ser Asn Ile Asn
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic fragment

<400> SEQUENCE: 24

Arg Pro Arg Asp Leu Ile Ser Asn Ile Asn Val Ile Val Leu Glu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic fragment

<400> SEQUENCE: 25

Ile Ser Asn Ile Asn Val Ile Val Leu Glu Leu Lys Gly Ser Glu
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic fragment

<400> SEQUENCE: 26

Val Ile Val Leu Glu Leu Lys Gly Ser Glu Thr Thr Phe Met Cys
1               5                   10                  15

<210> SEQ ID NO 27
<211> LENGTH: 15

```
<212> TYPE: PRT
<213> ORGANISM: Artificial Sequence
<220> FEATURE:
<223> OTHER INFORMATION: Synthetic fragment

<400> SEQUENCE: 27

Leu Lys Gly Ser Glu Thr Thr Phe Met Cys Glu Tyr Ala Asp Glu
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic fragment

<400> SEQUENCE: 28

Thr Thr Phe Met Cys Glu Tyr Ala Asp Glu Thr Ala Thr Ile Val
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic fragment

<400> SEQUENCE: 29

Glu Tyr Ala Asp Glu Thr Ala Thr Ile Val Glu Phe Leu Asn Arg
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic fragment

<400> SEQUENCE: 30

Thr Ala Thr Ile Val Glu Phe Leu Asn Arg Trp Ile Thr Phe Cys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic fragment

<400> SEQUENCE: 31

Thr Ala Thr Ile Val Glu Phe Leu Asn Arg Trp Ile Thr Phe Ser
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic fragment

<400> SEQUENCE: 32

Glu Phe Leu Asn Arg Trp Ile Thr Phe Cys Gln Ser Ile Ile Ser
1               5                   10                  15

<210> SEQ ID NO 33
<211> LENGTH: 15
<212> TYPE: PRT
```

```
<213> ORGANISM: Artificial Sequence
<220> FEATURE:
<223> OTHER INFORMATION: Synthetic fragment

<400> SEQUENCE: 33

Glu Phe Leu Asn Arg Trp Ile Thr Phe Ser Gln Ser Ile Ile Ser
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Synthetic fragment

<400> SEQUENCE: 34

Trp Ile Thr Phe Cys Gln Ser Ile Ile Ser Thr Leu Thr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic fragment

<400> SEQUENCE: 35

Trp Ile Thr Phe Ser Gln Ser Ile Ile Ser Thr Leu Thr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Synthetic fragment

<400> SEQUENCE: 36

Asn Arg Trp Ile Thr Phe Cys Gln Ser Ile Ile Ser Thr Leu Thr
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic fragment

<400> SEQUENCE: 37

Asn Arg Trp Ile Thr Phe Ser Gln Ser Ile Ile Ser Thr Leu Thr
1               5                   10                  15
```

IL-2 PEPTIDE DERIVATIVES, AND USES THEREOF FOR THE DIAGNOSIS AND TREATMENT OF AN AUTOIMMUNE DISEASE

FIELD OF THE INVENTION

The present invention relates to methods for the diagnostic of an autoimmune disease, to peptides and to treatment of autoimmune diseases.

BACKGROUND OF THE INVENTION

Type 1 diabetes (T1D) physiopathology is related to multiple defects in the interleukin-2 (IL-2) pathway that compromise regulatory T cell (Treg cell) homeostasis and therefore immune tolerance.

In humans with T1D, there is an urgent need for the development of novel biomarkers of ongoing autoimmunity, especially nowadays when there is a growing number of novel immunomodulatory therapies that could be offered to at-risk subjects during the prodromal phase, when treatment could be more effective. Novel biomarkers could help to better define such individuals with high-risk of developing T1D.

Today, measurement of IAA autoantibodies—hereinafter AutoAbs—(which precede T1D onset), and T-cell responses to pancreatic β-cell and to the presence of the susceptibility HLA-DQ8 and DQ2 alleles are used for the diagnostic of T1D.

WO2005094200 describes compositions and methods for differentiating between type 1 and type 2 diabetes by measuring levels of protein markers adiponectin and leptin and discloses that said protein markers are differentially present in the samples of patients suffering from type 1 diabetes, type 2 diabetes and/or diabetic disorders as compared to samples of control subjects. WO2005094200 also discloses methods and kits that can be used as an aid for diagnosis of type 1 diabetes, type 2 diabetes and/or diabetic disorders by detecting these protein markers. The measurement of these protein markers, alone or in combination, in patient samples provides information that a diagnostician can correlate with a probable diagnosis of-the extent of type 1 diabetes, type 2 diabetes and/or diabetic disorder.

SUMMARY OF THE INVENTION

The present inventors have discovered that anti-IL-2 AutoAbs (IL-2AAbs) with neutralizing capacity are associated to T1D. The inventors have further discovered that IL-2 AutoAbs are present at high frequencies in T1D, but also in systemic lupus erythematosus, rheumatoid arthritis, Sjögren's syndrome and autoimmune polymyositis patients.

The inventors have also observed that in T1D there is a loss of immune tolerance to IL-2, witnessed by the presence of IL-2 autoreactive T and B cells.

The inventors have further discovered that the autoreactive anti-IL-2 T-cell response in T1D is mainly directed to one specific epitope.

It is an object of the present invention to provide novel biomarkers of T1D and other autoimmune diseases.

DESCRIPTION OF THE PREFERRED EMBODIMENTS

Patients with autoimmune diseases, particularly T1D, systemic lupus erythematosus and rheumatoid arthritis patients display high frequencies of IL-2AAbs. HIL-2 AutoAbs are therefore biomarkers of such diseases.

A subject of the present application is therefore an in vitro method for determining whether a patient has, or is at risk of having or developing an autoimmune disease or for assessing the severity or predicting the outcome of an autoimmune disease, comprising a step of detecting or quantifying in a biological sample obtained from said patient an immune anti-IL2 response.

Immune anti-IL2 response may be evidenced by the detection of one or more of:
  B cells producing anti-IL2 AutoAbs;
  anti-IL2 antibodies;
  IL-2-specific T cells.

Preferred combinations of parameters are:
  B cells producing anti-IL2 AutoAbs and anti-IL2 antibodies,
  anti-IL2 antibodies and IL-2-specific T cells, and
  IL-2-specific T cells and B cells producing anti-IL2 AutoAbs A subject of the present application is particularly a method for determining in vitro whether a patient has, or is at risk of having or developing an autoimmune disease, comprising a step of detecting or quantifying the presence of AutoAbs in a biological sample obtained from said patient wherein the AutoAbs are anti-IL2 AutoAbs, particularly neutralizing anti-IL2 AutoAbs.

Quantifying the presence of neutralizing anti-IL2 AutoAbs in a biological sample obtained from a patient receiving IL2 as a therapeutic treatment for example allows adjusting the amount of IL2 administered and predicting the response of the patient to IL2 treatment.

Another subject of the present application is a method for predicting in a patient the outcome of an autoimmune disease, comprising a step of detecting or quantifying the presence of AutoAbs in a biological sample obtained from said patient wherein the AutoAbs anti-IL2 AutoAbs, particularly neutralizing anti-IL2 AutoAbs.

The autoimmune disease is preferably selected from the group consisting of type 1 diabetes (T1D), systemic lupus erythematosus (SLE), rheumatoid arthritis (RA), Sjögren's syndrome (SJO) and poymyositis (JO1) and is particularly type 1 diabetes.

Samples which may be used in the present methods are for example plasma, serum, whole blood, peripheral blood mononuclear cells (PBMCs), cytapheresis material, spleen cells, lymph node cells and bone marrow, supernatant of cultured immune cell and preferably serum and PBMCs.

Detecting the presence of B cells producing anti-IL-2 antibodies in a biological sample may be implemented according to methods well-known in the art such as B-cell ELISPOT, or by flow cytometry, and preferably B-cell ELISPOT.

Detecting the presence of AutoAbs in a biological sample may be implemented according to methods well-known in the art such as ELISA, competitive ELISA, or modified ELISAs (such as those using peptides/proteins coupled to biotin, or modified to detect IL-2/anti-IL-2Ab complexes), IL-2 neutralization using IL-2 responsive cells, IL-2 dependent cell lines, such as CTLL-2-based assay, Multiplex particle-based flow cytometry, liquid-phase immunoprecipitation, electrochemoluminescence, radioimmunoassay, and preferably immuno enzymatic methods.

Quantifying the presence of B cells producing anti-IL-2 antibodies in a biological sample may be implemented according to methods well-known in the art such as B-cell ELISPOT, or by flow cytometry Such a preferred method for example consists in Providing a sample, advantageously PBMCs, of a patient and performing B-cell ELISPOT to measure B cells producing anti-IL-2 antibodies Quantifying the presence of AutoAbs in a biological sample may also be implemented according to methods well-known in the art such as ELISA, competitive ELISA, or any modified ELISAs (such as those using peptides/proteins coupled to biotin), IL-2 neutralization using IL-2 responsive cells, IL-2 dependent cell lines, such as CTLL-2-based assay, Multiplex particle-based flow cytometry, liquid-phase immunoprecipitation, electrochemoluminescence, radioimmunoassay, and preferably immuno enzymatic methods.

Such a preferred method for example consists in

Providing a sample, advantageously serum of a patient and performing an ELISA test to measure anti-IL-2 antibodies.

Providing a sample, advantageously serum of a patient and performing a competitive ELISA test to measure anti-IL-2 antibodies.

Providing a sample, advantageously serum of a patient and performing an ELISA designed to measure IL-2/anti-IL-2 antibody immune complexes.

Providing a sample, advantageously serum of a patient and performing a multiplex particle-based flow cytometry test to measure anti-IL-2 antibodies Providing a sample, advantageously serum of a patient and performing an IL-2 neutralization test using IL-2 responsive cells and/or IL-2 dependent cell lines, such as CTLL-2-based assay to assess the presence of anti-IL-2 antibodies.

An object of the present invention is also a method for predicting/adjusting the response to exogenously administered IL-2 for therapeutic purposes comprising a step of detecting or quantifying in a biological sample obtained from said patient an immune anti-IL2 response.

For predicting the response of a patient to exogenously administered Il-2 (such as Proleukin® for example) the method preferably comprises the steps consisting in:

providing a biological sample obtained from said patient detecting the presence of anti-IL-2 antibodies (auto antibodies or antibodies detected against the exogenously administered IL-2) using any of the methods well-known in the art such as ELISA, competitive ELISA, or any modified ELISAs (such as those using peptides/proteins coupled to biotin), IL-2 neutralization using IL-2 responsive cells, IL-2 dependent cell lines, such as CTLL-2-based assay, Multiplex particle-based flow cytometry, liquid-phase immunoprecipitation, electrochemoluminescence, radioimmunoassay, and preferably immuno enzymatic methods.

or alternatively detecting the presence of IL-2/anti-IL-2 circulating complexes using, for example a specific ELISA to detect complexes or an ELISA including an step of dissociation of the complexes.

if the anti-IL-2 antibodies are present, for example with a value of AU obtained by ELISA, higher than the cut-off established for the technique, the amount of IL-2 to be administered to the patient should be adapted according to the desired immune response.

For adjusting the response of a treated patient to exogenously administered IL-2, the method preferably comprises the steps consisting in:

providing a biological sample obtained from said treated patient quantifying the presence of anti-IL-2 antibodies if anti-IL-2 Abs are higher than the cut-off defined for each technique, the amount of administered Il-2 has to be increased, and in the contrary, if anti-IL-2 antibodies are below the cut-off value, the amount of administered IL-2 does not have to be modified.

Alternatively, for adjusting the response of a treated patient to exogenously administered IL-2, the method would be adapted to the desired biological response, namely using low-dose IL-2 to increase the proportion of regulatory T cells, or, alternatively using high-dose IL-2 to increase the proportion of NK and CD8+T cells.

For example, in the case of administering IL-2 to increase regulatory T cell proportions, the amount of administered IL-2 should be adjusted in patients bearing anti-IL-2 antibodies to obtain a fixed increase in Tregs (for example an increase of 20% of the proportion of regulatory T cells in the blood, after IL-2 administration). Examples of treatments that could benefit from this IL-2 dose adjustment could be the treatment of graft-versus-host disease, in which IL-2 is administered at low-dose ($0.3 \times 10^6$, $1 \times 10^6$ or $3 \times 10^6$ IU/square meter of body-surface area, for 8 weeks followed by a 4 week hiatus) or at ultra low-dose IL-2 ($0.5 \times 10^6$, $1 \times 10^6$ or $2 \times 10^6$ IU/m2/day for 5 days);

Another example of treatment in which IL-2 administration in patients with anti-IL-2 antibodies could be adapted to obtain the fixed increase in Treg proportion is T1D (where IL-2 can be administered at ($1 \times 10^6$ or $3 \times 10^6$ IU/m$^2$/day for 5 days) or in autoimmune vasculitis (where Il-2 can be administered as 4 cycles of $3 \times 10^6$ IU/day for 5 days separated by 9 or 16-day washout)

The method would preferably comprise the steps consisting in providing a biological sample obtained from said treated patient, detecting the presence of anti-IL-2 antibodies, injecting IL-2 to the patients and defining the optimal dose based on the increase of regulatory T cell proportion obtained after 3 daily injections of IL-2.

For example, in the case of administering IL-2 to increase NK cell or CD8+T cell proportions, the amount of administered IL-2 should be adjusted in patients bearing anti-IL-2 antibodies to obtain a fixed increase in these populations. One example of such treatment is treatment of metastatic melanoma or renal cell carcinoma, where IL-2 is given at high-doses in different schedules (for example: administration of $6 \times 10^6$ IU/Kg every 8 hours by a 15 minutes intravenous infusion for a maximum of 14 doses).

The method would preferably comprise the steps consisting in providing a biological sample obtained from said treated patient, detecting the presence of anti-IL-2 antibodies, injecting IL-2 to the patients and defining the optimal dose based on the increase of NK cell or CD8+T cell proportion obtained after 3 daily injections of IL-2.

As previously mentioned, the inventors have further discovered that the autoreactive anti-IL-2 T-cell response in T1D is directed to any IL-2-derived peptide and is mainly directed to one specific epitope.

This is why the object of the present invention includes any peptide specifically recognised by anti-IL2 antibodies or IL-2-specific T cells of T1D, systemic lupus erythematosus, rheumatoid arthritis, Sjögren's syndrome and autoimmune polymyositis patients wherein said peptide is derived from IL-2, and particularly an IL-2 derived peptide of formula I

R1-LTRMLTFKFYMPKKA-R2     (I)

wherein

R1 represents the free or substituted primary amino function of the N-terminal amino acid, and R2 represents the free or substituted hydroxyl group of the carboxyl function of the C-terminal amino acid.

As used herein, the term "peptide" refers to an amino acid product having an amino acid sequence having at the least 6 amino acids and less than 50 amino acids, preferably less than 40 amino acids, more preferably less than 30 amino acids, particularly less than 25 amino acids, more particularly less than 20 amino acids.

The object of the present invention also includes the function-conservative variants of such peptides.

"Function-conservative variants" as used herein refer to those in which a given amino acid residue in a peptide has been changed (inserted, deleted or substituted) without altering the overall conformation and function (see above) of the peptide. Such variants include peptides having amino acid alterations such as deletions, insertions and/or substitutions. A "deletion" refers to the absence of one or more amino acids in the peptide. An "insertion" refers to the addition of one or more of amino acids in the peptide. A "substitution" refers to the replacement of one or more amino acids by another amino acid residue in the peptide.

Typically, a given amino acid is replaced by an amino acid with one having similar properties (such as, for example, polarity, hydrogen bonding potential, acidic, basic, hydrophobic, aromatic, and the like). Amino acids other than those indicated as conserved may differ in a peptide so that the percent protein or amino acid sequence similarity between any two peptides of similar function may vary and may be, for example, from 70% to 90% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, and still preferably at least 90%, and which has the same or substantially similar properties or functions as the native or parent peptide to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The object of the present invention also includes the function-conservative chemical derivatives of such peptides. A "function-conservative chemical derivative" also includes peptides chemically modified, preferably on R1 and R2 functions or on a lateral amino or carboxyl function of the peptide of formula I.

Preferred peptides of the invention are

```
                              SEQ ID No 1
        LTRMLTFKFYMPKKA

SEQ ID No 2
        EFLNRWITFSQSIIS
``` or a function-conservative variants of such peptides.

Concerning the variants, as is known by the person skilled in the art of immunology, modifications of the natural peptide chains are possible without however modifying the nature of the immunological properties of the immunogenic peptides. Derivatives of IL-2 peptides can therefore also be mentioned, which are highly homologous to these natural sequences, as previously mentioned whilst retaining the immunological properties of this epitopic site of the native peptide. Their homology zone can vary from 5 to 40 residues, for example from 8 to 40 residues, or also from 8 to 35 residues, preferably from 10 to 35 residues but also from 12 to 35 residues, notably from 12 to 30 residues, in particular from 15 to 30 residues and quite particularly from 15 to 25 residues.

The IL-2 peptide derivatives can contain modified residues, on condition that the modifications do not appreciably reduce the immunogenicity, either by adding chemical radicals (methyl, acetyl etc.) or by stereochemical modification (use of D series amino acids). The cytokine peptide derivatives should, like the IL-2 peptides induce antibodies interacting with IL-2.

The IL-2 peptide derivatives according to the invention can comprise one or more modifications in the amino acids of which they are constituted, such as deletions, substitutions, additions, or functionalizations (such as acylation) of one or more amino acids, to the extent that these modifications remain within the framework specified above (immunological characters). For example, in general the replacement of a leucine residue by an isoleucine residue does not modify such properties; the modifications should generally concern less than 40% of the amino acids, in particular less than 30%, preferably less than 20% and quite particularly less then 10% of the amino acids of the natural peptide. It is important that the antibodies induced by the modified peptides are active vis-à-vis native cytokine.

These modifications are within the scope of a person skilled in the art, who can verify the incidence of the modifications by simple tests. The immunogenicity of such modified derivatives can be evaluated by ELISA after immunization of mice, the antigen tested by ELISA being the entire cytokine or the immunizing cytokine peptide, or by cytokine-receptor bond blocking tests. The possible modifications preferably affect less than 8 amino acids, advantageously less than 6 amino acids, in particular less than 4 amino acids, and particularly 3 amino acids or less, such as 2 or 1 single amino acid.

A subject of the invention is also a compound characterized in that it contains at least one abovementioned cytokine peptide or cytokine peptide derivative. Such a compound can comprise identical peptide/derivative repetitions, or different peptide/derivative combinations, either in linear form or in the form of a candelabra structure or couplings mixed with carrier proteins. Such a compound can also be presented in cyclized form. Thus IL-2 peptides or IL-2 peptide derivatives according to the invention can for example be inserted into longer sequences of amino acids providing in particular a better conformation or combined with exogenous T epitopes (whether for protein or DNA immunizations).

They can advantageously be associated in a covalent manner with carrier proteins such as for example KLH.

These IL-2 peptides or IL-2 derivatives of the invention can be included in any protein sequence which comprises no homology with the other epitopes of natural IL-2. For example, they can be sites binding the receptor, to the ends of which a cysteine is simply added in order to confer a cyclic structure on the peptide. Another example is a peptide surrounded by sequences of T epitopes of the tetanus toxin. Yet another example can comprise a peptide corresponding to the sequence of the receptor binding site but where certain amino acids are replaced by their D series isomers in order to avoid their agonist effect.

In order to increase the immune response, the IL-2 peptides or IL-2 derivatives of the invention can be coupled to carrier proteins. The coupling methods and the carrier protein considered can be different according to the target peptide: they can for example be Keyhole Limpet Hemocyanin (KLH) protein and Tetanus Toxoid (TT) conjugated to the peptides by chemical methods well known to a person skilled in the art such as those of carbodiimide, glutaraldehyde or bis-diazotized benzidine coupling. The implementation of these couplings can be facilitated by the addition or incorporation of amino acids into the sequence, such as for example lysine, histidine, tyrosine or cysteine residues. Such peptide compounds coupled to an exogenous T epitope (originating from plasmodium falciparum, KLH, etc.) whether chemically or genetically also fall within the scope of the invention.

The peptides according to the invention can in particular be produced by chemical synthesis or genetic engineering or any other suitable method. The synthesis of cyclic peptides, grafting, as needed, one or more amino acids at the end of the chain as cysteines in order to create a disulphide bridge makes it possible to recover part of the secondary structure that these peptide fragments possess in the three-dimensional structure of the protein.

The peptides of the invention have advantageous properties. They are specifically recognized by T cells. They can therefore be used to detect an ongoing immune response mediated by T cells. They can also be used to induce tolerance to IL-2 in native form or in mutated IL-2 forms used for clinical purposes in humans. These properties are illustrated below in the experimental section. They justify the use of the peptides of the invention described above as a drug.

They can particularly be used as vaccines for generating IL-2 Abs from patients.

Preferred peptides of the invention are

```
                                          SEQ ID No 1
LTRMLTFKFYMPKKA

SEQ ID No 2
EFLNRWITFSQSIIS
``` or function-conservative variants of such peptides.

Detecting the presence of said peptide-specific T cells in a biological sample may be implemented according to methods well-known in the art such as measurement of T activation upon encounter of said peptides in vitro. Measurement of T cell activation can be done by methods such as measuring T cell proliferation by thymidine incorporation or cytokine production by ELISA, luminex or flow cytometry.

Quantifying the presence of IL-2-specific T cells in a biological sample may be implemented according to methods well-known in the art such as measuring T cell proliferation by thymidine incorporation or cytokine production by ELISPOT, ELISA, luminex or flow cytometry.

Such a preferred method for example consists in

Providing a sample, advantageously PBMCs, of a patient and performing an in vitro T cell activation assay using a library of peptides derived from the IL-2 sequence and measuring IFN-g production by ELISPOT Providing a sample, advantageously PBMCs, of a patient and performing an in vitro T cell activation assay using a library of peptides derived from the IL-2 sequence and measuring IFN-g production by cytometric bead array (CBA)

Providing a sample, advantageously PBMCs, of a patient and performing an in vitro T cell activation assay using a library of peptides derived from the IL-2 sequence and measuring thymidine incorporation The invention also relates to any peptide derived from IL-2, wherein said peptide is specifically recognised by anti-IL2 antibodies or IL-2-specific T cells of T1D, systemic lupus erythematosus, rheumatoid arthritis, Sjögren's syndrome and autoimmune polymyositis patients, and in particular an IL-2 derived peptide of formula I

R1-LTRMLTFKFYMPKKA-R2 (I)

wherein

R1 represents the free or substituted primary amino function of the N-terminal amino acid, and R2 represents the free or substituted hydroxyl group of the carboxyl function of the C-terminal amino acid, as well as function-conservative variants of such a peptide, for use in a method of therapeutic treatment of the human or animal body, that is to say as a drug.

Preferred peptides of the invention are

```
                                          SEQ ID No 1
LTRMLTFKFYMPKKA

SEQ ID No 2
EFLNRWITFSQSIIS
``` or a function-conservative variants of such peptides.

More particularly, the IL-2 protein or IL-2 derived peptides or a function-conservative variant thereof, and preferably the IL-2 derived peptides or a function-conservative variant thereof can be used for clinical purposes to induce tolerance to IL-2 in native form or in mutated IL-2 forms.

These properties and applications also justify the use of the peptides of the invention described above in a pharmaceutical composition.

As medicaments, an IL-2 peptide or IL-2 derivative of the invention can be incorporated into pharmaceutical compositions intended for any standard route in use in the field of vaccines, in particular by sub-cutaneous route, by intramuscular route, by intravenous route or by oral route. The administration can take place in a single dose or repeated once or more after a certain period of time.

The novel pharmaceutical compositions, in particular the vaccines, of the invention are comprised of an effective amount of at least one IL-2 peptide or preferably a peptide of formula I or of a function-conservative variant thereof and of an inert pharmaceutical carrier or excipient.

A subject of the present application is also a curative or preventative pharmaceutical composition, characterized in that it comprises as active ingredient, one or more IL2 peptides or IL2 derivatives as defined above.

The immunogenic agent can be conditioned alone or mixed with an excipient or mixture of pharmaceutically acceptable excipients as an adjuvant. A subject of the present application is more particularly a vaccine containing as immunogen, an abovementioned IL-2 peptide or IL-2 derivative.

A subject of the present invention is also a process for preparing a composition described above, characterized in that, according to methods known per se, the active ingredient or ingredients are mixed with acceptable, in particular pharmaceutically acceptable excipients.

Since they can be used to induce tolerance to IL-2, the novel compositions of the invention are useful for example in both the curative and preventive treatment of immune mediated disease, for example, in the treatment of autoimmune diseases and in the treatment of inflammatory disease. They can also be used in the treatment of T1D as well as in the treatment of SLE. They can also be used in the treatment of RA, SJO, JO-1, MS.

The usual dose, which varies depending on the subject and the condition in question, may be, for example, from 1 to 1000 µg, in particular 10 to 500 µg, by sub-cutaneous route, once a month for three months, then periodically as a function of the induced serum antibodies count, for example every 2-6 months of the peptide LTRMLTFKFYMPKKA (seq Id No 1), for the treatment of RA, SJO, JO-1, MS.

This is why the object of the present invention is also any peptide derived from IL-2, wherein said peptide is specifically recognised by anti-IL2 antibodies or IL-2-specific T cells of T1D, systemic lupus erythematosus, rheumatoid arthritis, Sjögren's syndrome and autoimmune polymyositis patients, and in particular an IL-2 derived peptide of formula I

R1-LTRMLTFKFYMPKKA-R2     (I)

wherein
R1 represents the free or substituted primary amino function of the N-terminal amino acid, and
R2 represents the free or substituted hydroxyl group of the carboxyl function of the C-terminal amino acid,
as well as function-conservative variants of such peptides, for use in a method of therapeutic treatment of autoimmune diseases and in the treatment of inflammatory diseases.

Autoimmune diseases are preferably T1D as well as SLE. The peptides of the invention can also be used in the treatment of RA, SJO, JO-1 and MS.

Preferred peptides of the invention are

```
                                           SEQ ID No 1
        LTRMLTFKFYMPKKA

SEQ ID No 2
        EFLNRWITFSQSIIS
```

B cells producing anti-IL2 antibodies or AutoAbs may be used for manufacture of anti-IL-2 antibodies. Said anti-IL-2 antibodies may be used for research, diagnostic or for clinical applications as previously explained.

Anti-IL2 antibodies may be manufactured according to standard methods such as immortalization of the corresponding B-cell clones and recovering the anti-IL2 antibodies produced by the hybridomas, or by generating recombinant antibodies based on DNA products obtained from subjects having B cells producing anti-IL2 antibodies or anti-IL-2 AutoAbs.

A further object of the present invention is therefore the use of anti-IL-2 antibodies or AutoAbs obtained according to the above methods in an above-mentioned diagnostic or clinical application.

The following examples illustrate the present invention.

Preferred conditions for implementing the methods described above also apply to the other subjects of the invention envisaged above.

The scope of the invention can be understood better by referring to the examples given below, the aim of which is to explain the advantages of the invention.

EXPERIMENTAL DATA

Figure 1:
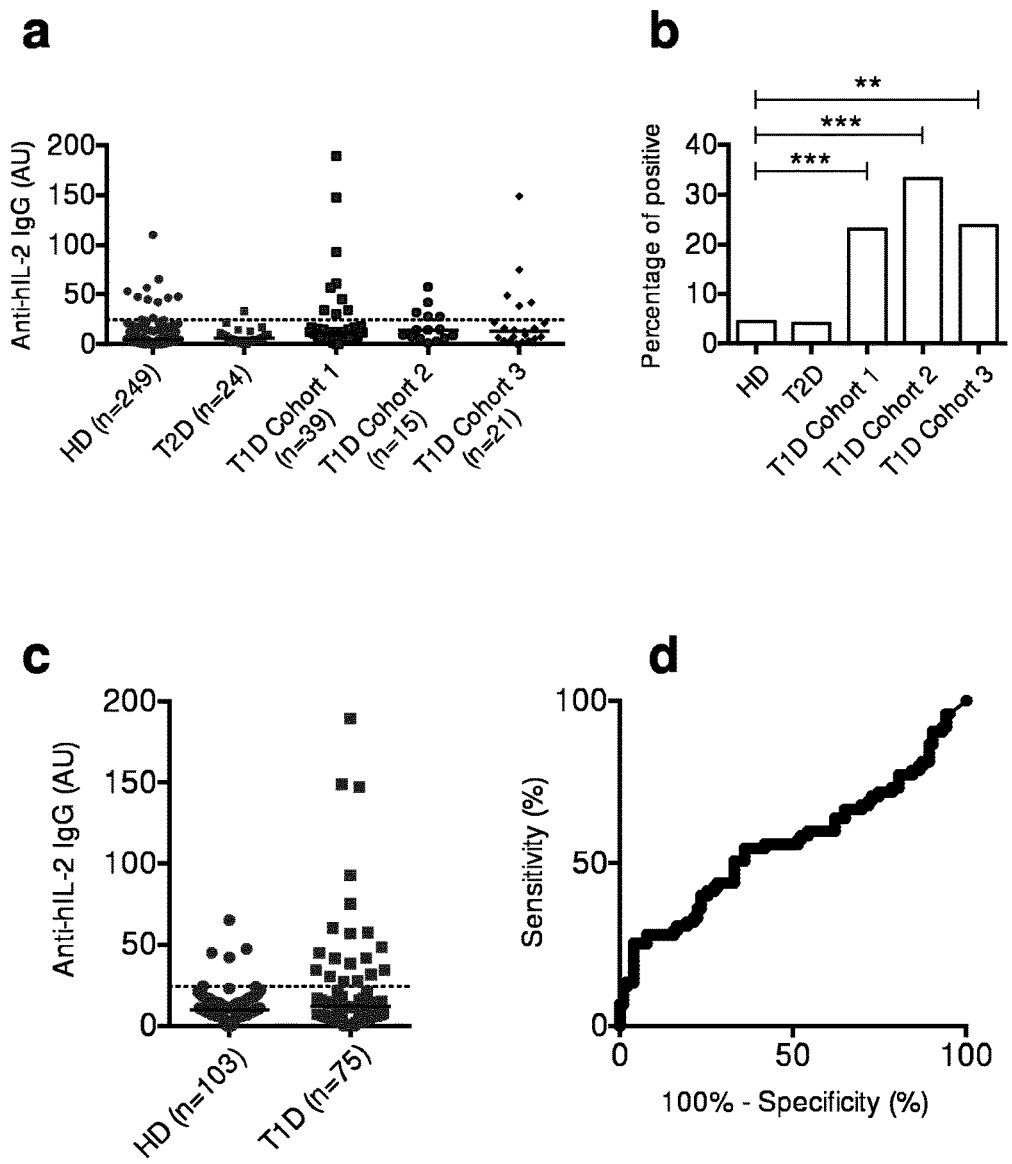
FIGS. 1a and b respectively represent the serum titres of anti-hIL-2 IgG autoAbs in different groups of patients and the percentage of hIL-2A positive patients in the different groups of patients, measured by ELISA.
FIGS. 1c and d are done with a pool of healthy donors and a pool of T1D patients to establish the cut-off of positivity for the ELISA determination of anti-IL-2 autoAbs. Panels c and d show ELISA results for anti-IL2 autoAbs and figure d shows the ROC curve used to determine the cut-off in a experiment of quantification of IL-2 AutoAbs by ELISA.

The human serum and plasma samples used are described hereunder.

1. Sera samples were obtained from healthy donors (HD; n=249) and from patients suffering from type 2 diabetes (T2D; n=24), type 1 diabetes (T1D; n=39 in cohort 1, n=15 in cohort 2 and n=21 in cohort 3).

Adult healthy donors, T2D or T1D (cohort 1) patients were recruited at the Diabetology Unit of the Pitié Salpêtrière Hospital in Paris (France) following the local ethic guidelines. Serum samples from healthy donors and T1D (cohort 2) patients were provided by the DASP program (http://www.cdc.gov/labstandards/diabetes_dasp.html). Healthy donors and T1D patients from cohort 3 were recruited at the San Raffaele Institute in Milan (Italy), following the local ethic guidelines. Only adult T1D patients were included in the final analysis.

2. Healthy donors matched with patients suffering from different inflammatory/autoimmune diseases were recruited at INSERM U905, Rouen (France). For this cohort, patients were classified according to established classification criteria: ACR revised criteria for SLE with anti-dsDNA AutoAbs, ARA criteria for RA with anti-CCP antibodies and/or rheumatoid factor, revised European criteria for primary Sjögren's syndrome with anti-SSA and/or anti-SSB AutoAbs, Troyanov criteria for overlap myositis with anti-tRNA-synthetase Jo-1 autoantibody, and described previously.

Patients suffering from MS according to the 2005 McDonald criteria and chronic inflammatory demyelinating polyneuropathy (CIDP) according to EFNS criteria, were recruited at Henri Mondor Hospital/UPEC University, Créteil (France). Sera were collected before initiation of methylpredinisolone in case of relapse of MS and before initiation of intravenous immunoglobulin treatment in case of CIDP. This retrospective study received ethical standards committee approval, and patients were informed of the collection of their anonymous data for research according to French standards.

Sera from patients suffering from different cancers (melanoma, head and neck, lung, colo-rectal or breast) were obtained from the Centre de Ressources Biologiques at the Curie Institut Paris (Dr. S. Saada), in accordance with the Local Ethical Guidelines.

All serum samples were kept at −20° C. or −80° C. until use.

Example 1. Quantification of Anti-Human IL-2 AutoAbs in Human Serum and Plasma Samples—Diabetes Serum titers of hIL-2AAb were assessed by ELISA. Microtiter 96-well plates (Medisorp, Nunc) were incubated overnight at 4° C. with 100 µl/well of carbonate coating buffer containing $10^5$ IU/ml hIL-2 ("IL-2 coated wells") or buffer alone ("uncoated wells", blank). After blocking with PBS/2% BSA for 2 h, plates were incubated with 50 µl serially diluted serum samples for 2 h at room temperature. After extensive washing with PBS/0.1% Tween20, HRP-conjugated anti-human IgG (1:2,000; Dako) was added to each well and the plates were kept at room temperature for 1 h. Peroxidase activity was measured with TMB substrate as before. Standard curve was generated using two-fold serial dilutions of rat anti-human IL-2 (clone MQ1-17H12, eBioscience) revealed with an HRP-conjugated goat anti-rat Ig. Arbitrary Units for each sample were calculated using the O.D. value obtained after subtraction of the blank. For human competition assays, sera from hIL-2AAb− healthy donors or from hIL-2AAb+ patients (diluted 1/100, 1/200 or 1/300) were pre-incubated with increasing concentrations of hIL-2 for 1 h at room temperature. Samples were then added to the ELISA plate and the plate processed as above.

Results:

The results of serum titres of anti-hIL-2 IgG in the different groups of patients and the percentage of hIL-2A positive patients in the different groups of patients are shown in FIGS. 1a and 1b (Ex FIG. 5a,b). Dashed line of left graphs indicates the threshold of positivity. Symbols represent individual subjects and horizontal bars are the medians. P<0.01; *P<0.001 (Fisher exact test). For ELISA tests quantifying hIL-2AAbs, we fixed the threshold of positivity at a value of 24.3 AU, which allowed discrimination of healthy donors and T1D subjects with 95% specificity. This cut-off was calculated with a ROC curve with a 95% confidence interval, using the T1D subjects of cohorts 1, 2 and 3 (n=75), as patients; and the healthy donors coming from these cohorts (n=103), as controls (FIG. 1c-d).

Significantly increased percentages of sera from T1D patients were hIL-2AAb+ (23.1, 33.3 and 23.8% in cohorts 1, 2 and 3; respectively), compared to the low percentages observed in healthy donors (4.4%) and T2D patients (4.2%).

Conclusion

The results of percentage of anti-hIL-2 positive subjects among the different cohorts (right graphs) evidence that IL-2 AutoAbs are present at high frequencies in type 1 diabetes.

Therefore, anti-hIL-2 antibodies may be used as markers of type 1 diabetes.

Example 2. Human IL-2 ELISA Competition Assay

Microtiter 96-well plates (Medisorp, Nunc) were incubated overnight at 4° C. with 100 µl/well of carbonate coating buffer containing $10^5$ IU/ml hIL-2 ("IL-2 coated wells") or buffer alone ("uncoated wells", blank). After blocking with PBS/2% BSA for 2 h, plates were incubated for 2 h at room temperature with 50 µl serially diluted serum samples pre-incubated or not with increasing concentrations of hIL-2 for 1 h at room temperature. After extensive washing with PBS/0.1% Tween20, HRP-conjugated anti-human IgG (1:2,000; Dako) was added to each well and the plates were kept at room temperature for 1 h. Peroxidase activity was measured with TMB substrate as before. Standard curve was generated using two-fold serial dilutions of rat anti-human IL-2 (clone MQ1-17H12, eBioscience) revealed with an HRP-conjugated goat anti-rat Ig. Arbitrary Units for each sample were calculated using the O.D. value obtained after subtraction of the blank.

Figure 2:
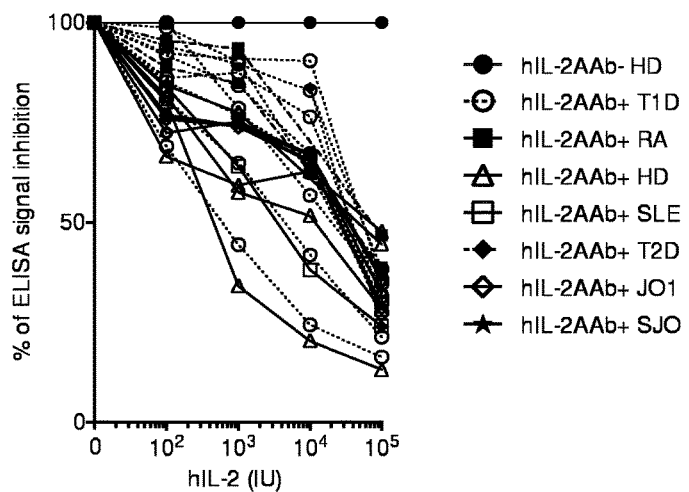
FIG. 2 shows the results of a competition ELISA assay performed with human IL-2 in healthy donors, T2D patients and five auto immune diseases. Results are expressed as a percentage of ELISA signal inhibition according to the amount of human IL-2

The results are shown in FIG. 2

The results evidence that the ELISA signal of the coloured substrate decreases according to a hIL-2 dose-dependent pattern for type 1 diabetes, systemic lupus erythematosus and rheumatoid arthritis. Therefore, the antibodies are IL-2 specific.

Example 3. Detection of B-Cells Producing Anti-IL-2 AutoAbs by Mice—Elispot

After activation with 35% ethanol, 96-well PVDF plates (MAIP4510, Millipore) were coated with 70 µL/well of 5 µg/mL mIL-2 (Peprotech) overnight at 4° C. After washing with PBS, plates were blocked with Protein-Free Blocking Buffer (Thermo) for 1 h at room temperature and then with complete RPMI medium for 30 min at room temperature. Serially diluted spleen or bone marrow cells ($5 \times 10^4$ to $4 \times 10^5$ cells per well in complete RPMI medium) from 10- to 18-week-old female B6 or NOD mice were added in the ELISPOT plate. In a set of experiments, splenocytes from 10- to 18-week-old female B6 or NOD mice were cultured for 6 days at $1 \times 10^6$ cells/mL in complete RPMI medium with 10 µg/mL CpG-ODN 1018 to allow expansion of memory B cells. Serially diluted CpG pre-activated splenocytes ($5 \times 10^4$ to $4 \times 10^5$ cells per well) were then added in the ELISPOT plate. After a 18 h culture, plates were washed 3 times with PBS/0.25% Tween-20, 3 times with PBS and then incubated with alkaline phosphatase-anti-mouse-IgG (1:1,000; Sigma-Aldrich) diluted in PBS/2% BSA for 2 h at room temperature. Plates were then washed and phosphatase activity measured adding 100 µL/well substrate (Bio-Rad).

Reaction was blocked by extensive washing with tap water after 15 min incubation. Spots were counted with an AID camera.

Figure 3:
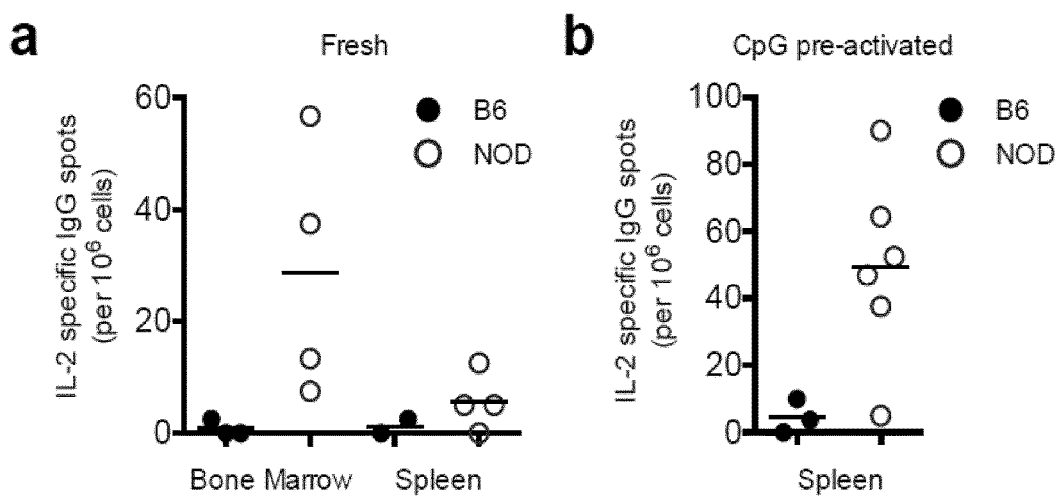
FIGS. 3 a and b respectively represent the results of ELISPOT assays. The number of IL-2 specific IgG spots per $10^6$ cells is given according to the type of mouse (NOD or B6) and of the nature of the cell tissue (spleen or bone marrow).

The results are shown in FIGS. 3a and 3b

B lymphocytes producing anti-IL-2 antibodies are detected only in NOD mice.

Conclusion

The above results evidence that techniques such as B cell Elispot may be used in humans for the detection of production of anti-IL-2 antibodies by B cells.

Example 4. Quantification of Anti-Human IL-2 AutoAbs in Human Serum and Plasma Samples—Other Auto-Immune Diseases Serum samples were obtained from healthy donors (HD, n=249), T1D (n=75 in the three pooled cohorts), multiple sclerosis (MS; n=33), Sjögren syndrome (SJO; n=22), anti-JO1 positive polymyositis (JO1; n=16), rheumatoid arthritis (RA; n=33), systemic lupus erythematosus (SLE; n=20), chronic inflammatory demyelinating neuropathy (CIPD; n=51) and cancer (Cancer; n=128) patients. (a) Serum titers of anti-hIL-2 IgG in the different cohorts. Dashed line indicates the threshold of positivity (set as the same value as in example 1). (b) percentage of anti-hIL-2 positive subjects among the different cohorts. Symbols represent individual subjects and horizontal bars are the medians. *$P<0.05$; ***$P<0.001$ (Fisher exact test).

Figure 4:
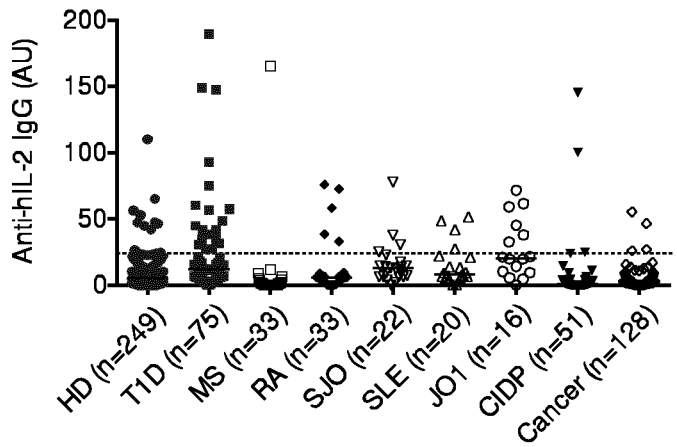
FIGS. 4 a and b respectively represent the serum titres of anti-hIL-2 IgG autoAbs in different groups of patients and the percentage of hIL-2A positive patients in the different groups of patients.
Figure 4:
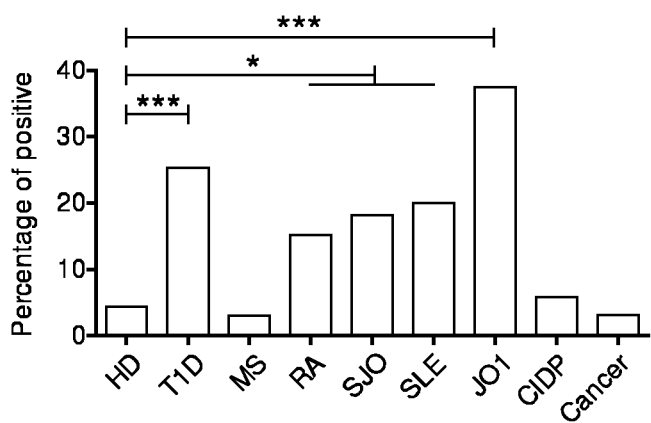

The results are shown in FIG. 4.

Both graphs show that like T1D patients, SLE, RA, SJO and JO-1 patients display high frequencies of hIL-2AAbs.

Conclusion

Since patients with SLE, RA, SJO and J0-1 display high frequencies of hIL-2A, the above results evidence that hIL-2A is a biomarker of such diseases Example 5. Quantification of IL-2 Specific T Cells by CBA IFN-g production by 10-18 week-old female B6 (n=3) or pre-diabetic NOD (n=7) splenocytes was quantified in culture supernatants by CBA after 72 h of stimulation with DMSO, mIL-2 peptides that gave a positive response in the initial screen (3 and 10 μmol/L of each peptide), P31 peptide (3 and 10 μmol/L) or aCD3-CD28 coated beads (ratio 1bead:1cell). Symbols represent individual mice. Data are cumulative of two independent experiments.

Figure 5:
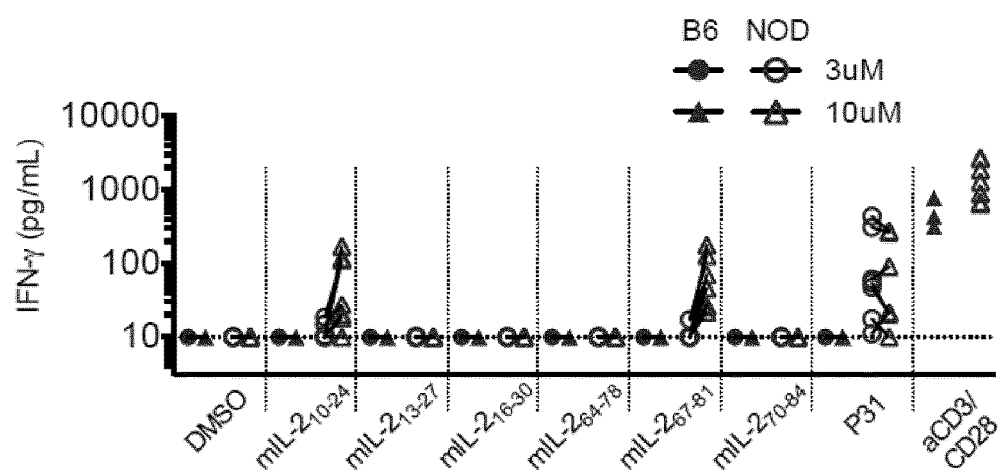
FIG. 5 represents IFN-g production measured by CBA in the supernatant of splenocytes responding to IL-2-derived peptides.

The results are shown in FIG. 5.

The results show that only two peptides derived from the mIL-2 sequence can induce IFN-g production by NOD splenocytes but not by B6 splenocytes.

Conclusion

Since NOD mice present IL-2 specific T cells (reactive to two different peptides), the above results evidence that IL-2 specific T cells (detected by IFNg CBA after re-stimulation with IL-2 peptides) could be used as a biomarker of T1D.

Example 6. Quantification of IL-2 Specific T Cells by ELISPOT

The following human IL-2 peptide library was prepared: 21.

| Peptide ID | Sequence |
| --- | --- |
| hIL-2$_{1-15}$ | MYRMQLLSCIALSLA |
| hIL-2$_{6-20}$ | LLSCIALSLALVTNS |
| hIL-2$_{11-25}$ | ALSLALVTNSAPTSS |
| hIL-2$_{16-30}$ | LVTNSAPTSSSTKKT |
| hIL-2$_{21-35}$ | APTSSSTKKTQLQLE |
| Pro$_{1-15}$ | MPTSSSTKKTQLQLE |
| hIL-2$_{26-40}$ | STKKTQLQLEHLLLD |
| hIL-2$_{31-45}$ | QLQLEHLLLDLQMIL |
| hIL-2$_{36-50}$ | HLLLDLQMILNGINN |
| hIL-2$_{41-55}$ | LQMILNGINNYKNPK |
| hIL-2$_{45-60}$ | NGINNYKNPKLTRML |
| hIL-2$_{51-65}$ | YKNPKLTRMLTFKFY |
| hIL-2$_{56-70}$ | LTRMLTFKFYMPKKA |
| hIL-2$_{61-75}$ | TFKFYMPKKATELKH |
| hIL-2$_{66-80}$ | MPKKATELKHLQCLE |
| hiL-2$_{71-85}$ | TELKHLQCLEEELKP |
| hIL-2$_{76-90}$ | LQCLEEELKPLEEVL |
| hIL-2$_{81-95}$ | EELKPLEEVLNLAQS |
| hIL-2$_{86-100}$ | LEEVLNLAQSKNFHL |
| hIL-2$_{91-105}$ | NLAQSKNFHLRPRDL |
| hIL-2$_{96-110}$ | KNFHLRPRDLISNIN |
| hIL-2$_{101-115}$ | RPRDLISNINVIVLE |
| hIL-2$_{106-120}$ | ISNINVIVLELKGSE |
| hIL 2$_{111-125}$ | VIVLELKGSETTFMC |
| hIL-2$_{116-130}$ | LKGSETTFMCEYADE |
| hIL-2$_{121-135}$ | TTFMCEYADETATIV |
| hIL-2$_{126-140}$ | EYADETATIVEFLNR |
| hIL-2$_{131-145}$ | TATIVEFLNRWITFC |
| Pro$_{111-125}$ | TATIVEFLNRWITFS |
| hIL-2$_{136-150}$ | EFLNRWITFCQSIIS |
| Pro$_{116-130}$ | EFLNRWITFSQSIIS |
| hIL-2$_{141-153}$ | WITFCQSIISTLT |
| Pro$_{121-133}$ | WITFSQSIISTLT |
| hIL-2$_{139-153}$ | NRWITFCQSIISTLT |
| Pro$_{129-133}$ | NRWITFSQSIISTLT |

IFN-g production by PBMCs from HD (n=14, closed circles) or T1D patients (n=13, open circles) was quantified by ELISPOT after stimulation with hIL-2 or Proleukin (Pro) peptides (10 μM/each) that gave a positive response in the initial pool screening, intracellular IA-2, adenovirus lysate (AdV) or PHA. The number of IFN-g spot-forming cells (SFC)/10$^6$ PBMCs is depicted, the dashed line indicates the positive cutoff and the grey shaded area shows undetectable responses (i.e. identical to spontaneous background responses; see material and methods for threshold determination). The percent of positive T1D (top number) and HD (bottom number) is indicated for each condition, with antigens yielding responses significantly different between HD and T1D patients in bold (P<0.03 by Fisher exact test).

Figure 6:
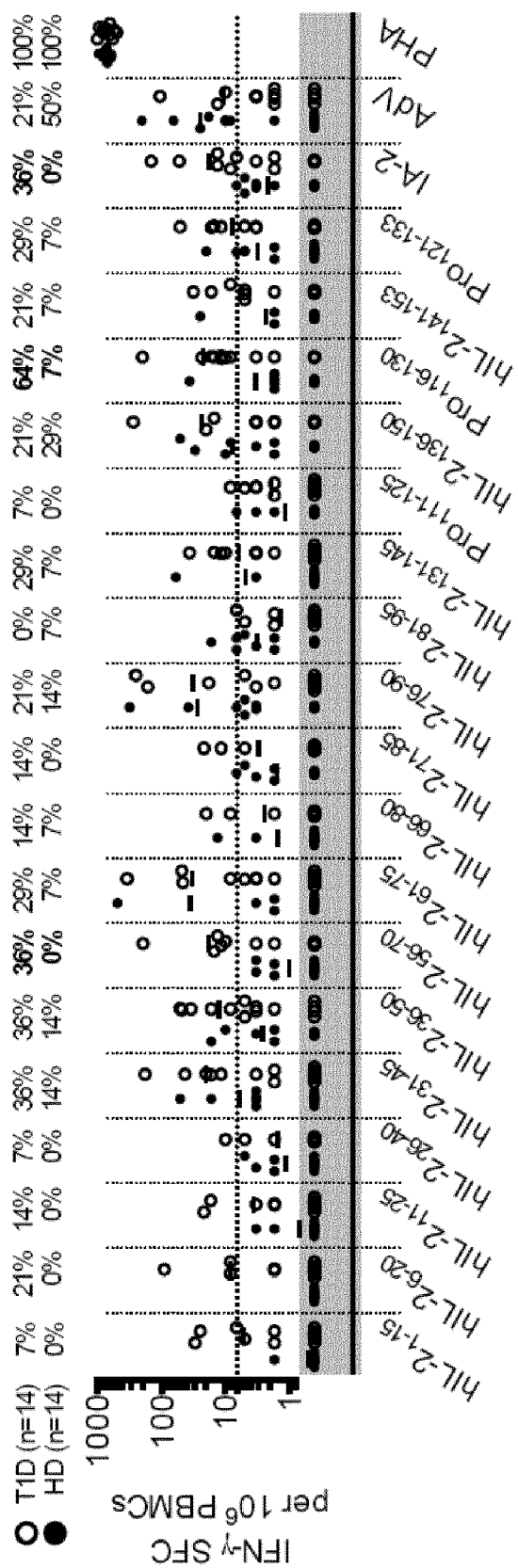
FIG. 6 represents the results of ELISPOT assays. The number of IFN-γ spot-forming cells (SFC)/$10^6$ PBMCs after background subtraction is given after stimulation of PBMCs with different IL-2 peptides and other control peptides.

The results of are shown in FIG. 6.

The results show that only one peptide derived from the hIL-2 sequence can induce IFN-g production by T1D PBMCs but not by HD PBMCs.

The results also show that the peptide EFLNRWITF-SQSIIS abbreviated Pro116-130, said peptide being derived from the hIL-2 sequence of the Proleukin® protein, can induce IFN-g production in a significantly higher frequency of T1D PBMCs compared to HD PBMCs.

Conclusion

Since T1D patients present IL-2 specific T cells (reactive to many, but specifically to one peptide), the above results evidence that IL-2 specific T cells (detected by IFNg ELISPOT after restimulation with IL-2 peptides) could be used as a biomarker of T1D.

Additionally, peptides such as peptide EFLNRWITF-SQSIIS derived from the hIL-2 sequence may be used to detect an immune response anti exogenously administered IL-2, Proleukin in this particular case.

Example 7. Quantification of IL-2/IL-2A Immune Complexes by ELISA

Mice were bled from the retro-orbital sinus, and serum titers of IL-2/IL-2AAb immune complexes quantified by ELISA. Microtiter 96-well plates (Medisorp, Nunc) were incubated overnight at 4° C. with 100 µl/well of carbonate coating buffer (pH 9.6) containing 0.5 µg/mL polyclonal anti-mIL-2 (PeproTech). After blocking with PBS/2% BSA for 2 h, plates were incubated with 50 µl of serially diluted sera in duplicate for 2 h at room temperature. After extensive washing with PBS/0.1% Tween20, biotin-labeled antimouse IgG (1:5,000; Southern Biotech) was added to each well and the plates were kept at room temperature for 1 h. Plates were subsequently incubated with horseradish peroxidase (HRP)-conjugated streptavidin (1:2,000; Invitrogen) for 30 min followed by TMB substrate (eBioscience or BD Biosciences) for 10 minutes. The reaction was acid blocked and absorbances were read at 450 nm with a DTX 880 Multimode Detector (Beckman Coulter).

Figure 7:
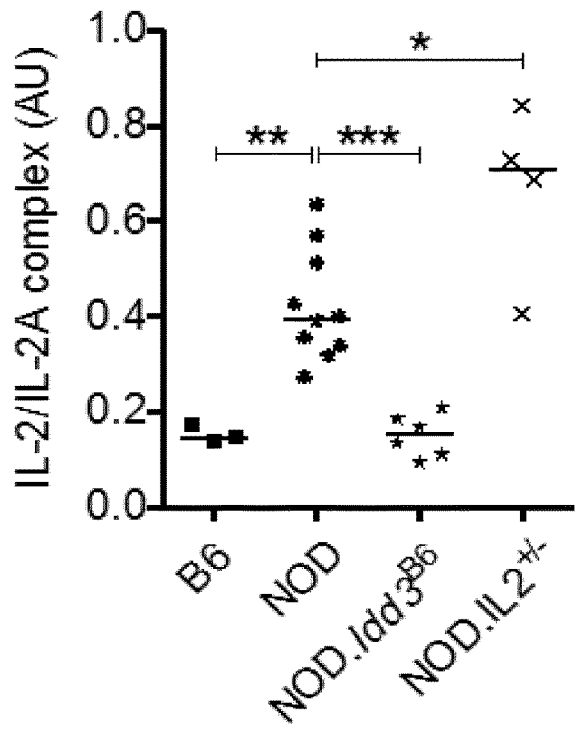
FIG. 7 shows the results of serum titres of IL-2/IL-2A complexes in different mouse strains in an ELISA assay.

The results are given in FIG. 7.

Legend

Serum samples were obtained from different mouse strains (all females and age-matched): B6, wild type NOD, NOD.Idd3$^{B6}$, Il-hemizygous NOD: NOD.Idd3$^{NOD/NOD-IL-2null}$ (NOD.Il2$^{+/-}$). Serum titers of IL-2/IL-2AAb complex (b) in the different mouse strains. Symbols represent individual mice and horizontal bars are the medians. ns, not significant. *P<0.05; P<0.01; *P<0.001 (non-parametric Mann-Whitney test).

Figure 10:
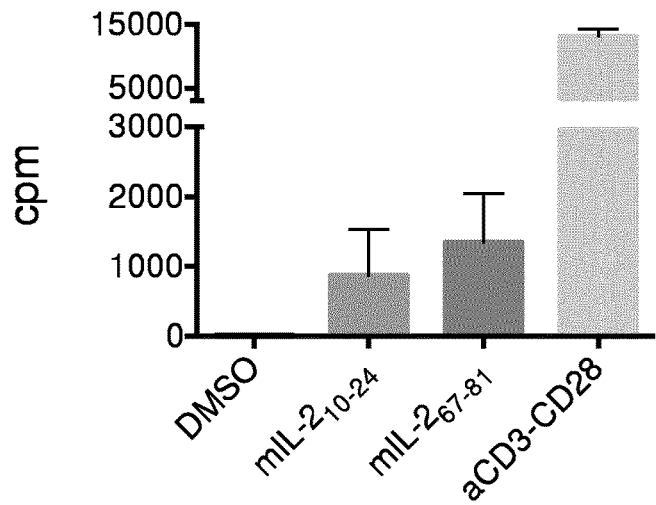
FIG. 10 shows the results of a quantification of IL-2 specific T cells by proliferation assay.

As can be seen on FIG. 10, NOD mice present higher titers of IL-2/IL-2A immune complexes than B6 mice.

Conclusion:

Since NOD display high titres of IL-2/IL-2A immune complexes (as detected by ELISA), the above results evidence that IL-2/IL-2A immune complexes (as here detected by ELISA) could be used as a biomarker of T1D.

Example 8. Quantification of IL-2 AutoAbs by Multiplex Particle-Based Flow Cytometry Recombinant mIL-2 was covalently coupled to carboxylated beads (Bio-Rad Laboratories). Beads were first activated with 1-ethyl-3-[3-dimethylaminopropyl]carbodiimide hydrochloride in the presence of N-hydroxysuccinimide (Thermo Fisher), according to the manufacturer's instructions, to form amine-reactive intermediates. The activated beads were incubated with 10 µg/mL mIL-2 in the reaction mixture for 2 h at room temperature under rotation. Beads were then blocked and stored according to the manufacturer's instructions. Coupling was verified using a commercial anti-mIL-2 monoclonal antibody (clone JES6-1A12, eBioscience), biotin-anti-rat Ig (BD Biosciences) and then PE-streptavidin (Invitrogen). mIL-2-coupled beads were incubated with serially diluted sera from B6 or NOD mice for 2 h in 96-well plates at room temperature in the dark on a horizontal shaker. Beads were washed twice with PBS/0.05% Tween-20 and incubated for 1 h with a biotin-labeled antimurine IgG antibody (1:250; Southern Biotech), washed, incubated 30 min with PE-streptavidin (1:125; Invitrogen), washed again and resuspended in 100 µL PBS/0.05% Tween-20. Beads were then analyzed on LSRII flow cytometer (BD Biosciences) and data analyzed with FlowJo software. For mIL-2AAbs competition assays, sera from B6 or NOD mice (diluted 1/10) were pre-incubated with increasing concentrations of mIL-2 for 2 h at room temperature. mIL-2 coated beads were then added and multiplex particle-based flow cytometry processed as described above.

Figure 8:
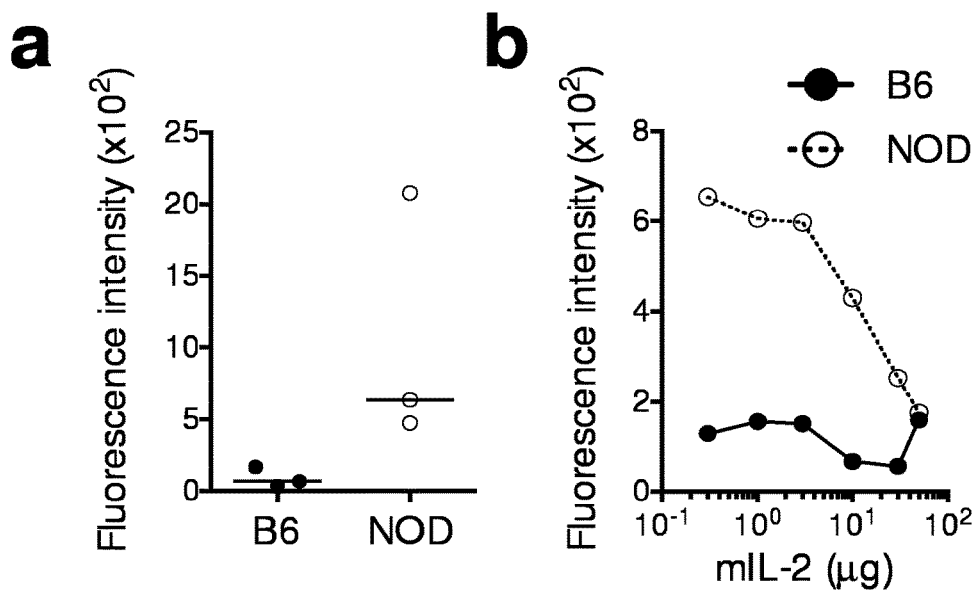
FIGS. 8 a and b show the results of a quantification of IL-2 AutoAbs by multiplex particle-based flow cytometry. Results are expressed as a fluorescence intensity in different mouse strains and in a competition assay pre-incubating the sera with different amounts of mIL-2.

The results are given in FIG. 8.

Titers of anti-murine-IL-2 IgG were quantified by FACS with IL-2 coated fluorescent beads. (b) Competition assay: sera from an anti-mIL-2 negative B6 mouse (closed circles) or from an anti-hIL-2 positive pre-diabetic NOD mouse (open circles) were pre-incubated for 1 h with increasing amounts of free recombinant mIL-2 and titers of anti-mIL-2 were then quantified by FACS with IL-2 coated fluorescent beads. Symbols represent individual mice and horizontal bars are the medians. Data are cumulative of at least two independent experiments.

As can be seen on FIG. 8a, NOD mice but not B6 mice present higher titers of mIL-2AAbs as detected by multiplex particle-based flow-cytometry.

As can be seen on FIG. 8b, mIL-2AAbs detected by multiplex particle-based flow-cytometry in the serum of NOD mice are specific.

Conclusion:

Since multiplex particle-based flow-cytometry allows the detection of specific IL-2AAbs, the above results evidence that IL-2AAbs (detected by multiplex particle-based flow-cytometer competition multiplex particle-based flow-cytometry) could be used as a biomarker of T1D.

Example 9. Study of the Neutralizing Capacity of IL-2 AutoAbs by Neutralization Assay CTLL-2 cells (ATCC, mycoplasma-free) were cultured (104 cells/well) in 96-well plates in complete RPMI medium (Gibco) containing no mIL-2, 1 ng/mL mIL-2 or 3 IU/mL hIL-2 with or without heat-inactivated (30 min at 56° C.) serially diluted serum from B6 or NOD mice. After 48 h, cultures were pulsed 18 h with [3H]-thymidine (1 µCi/well) and counted by liquid scintillation.

Figure 9:
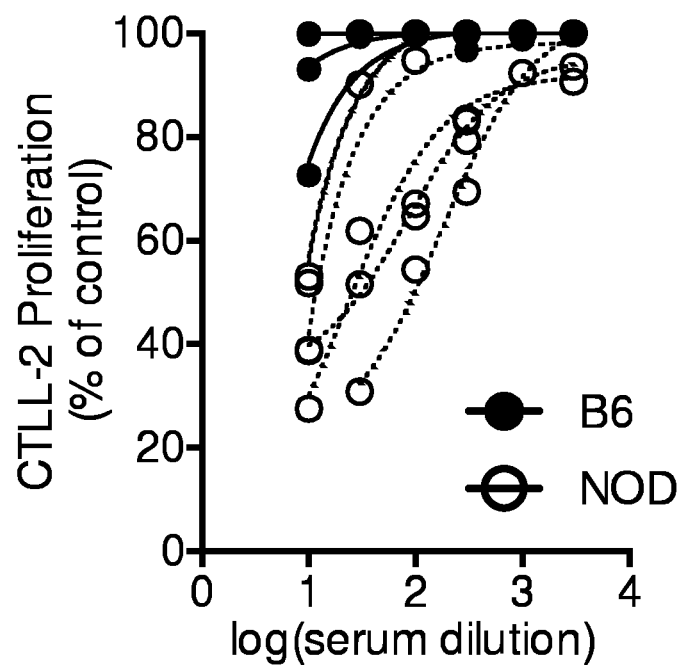
FIG. 9 shows the results of the evaluation of the neutralizing capacity of IL-2 AutoAbs in a neutralisation assay. Results are expressed as % of proliferation of CTLL-2 cells in comparison with the control as a function of the serum dilution.

The results are given in FIG. 9.

Legend

Proliferation of CTLL-2 cells cultured for 3 days with 1 ng/mL mIL-2 and different concentrations of B6 (closed circles) or NOD (open circles) sera. Proliferation is expressed as percentage of control (CTLL-2 cultured for 3 days with 1 ng/mL mIL-2 without mouse serum). Symbols and curves represent individual mice and horizontal bars are the medians. Data are cumulative of at least two independent experiments.

As can be seen on FIG. 9, the growth of the IL-2 dependent cell-line CTLL-2 is inhibited only by NOD serum but not by B6 serum; indicating that NODmice present neutralizing IL-2AAbs.

Conclusion:

Since CTLL-2-based neutralization assays allows the detection of neutralizing IL-2AAbs, the above results evidence that neutralizing IL-2AAbs (detected by in vitro neutralization assay) could be used as a biomarker of T1D.

Example 10. Quantification of IL-2 Specific T Cells by Proliferation Assay

A peptide library of 15-mers overlapping by 12 amino acids covering the whole sequence of mIL-2 (including the signal peptide) was generated (GL-Biochem). Peptides (10 mmol/L) were stored in DMSO at −20° C. until use. Splenocytes from 10- to 18-week-old female NOD mice were cultured in triplicate ($4\times10^5$ cells/150 µL/well) in X-Vivo 15 serum-free medium (Lonza) containing DMSO (negative control), aCD3-CD28 beads (positive control, ratio 1bead:1cell, Life Technologies) or peptides (10 µmol/L). After 96 h, cultures were pulsed 18 h with [3H]-thymidine (1 µCi/well) and counted by liquid scintillation.

The results are given in FIG. 10

Legend

Proliferation (cpm) by 10-18 week-old female pre-diabetic NOD (n=3) splenocytes was quantified by thymidine incorporation after 96 h of stimulation with DMSO, mIL-2 peptides that gave a positive response in the initial screen (10 µmol/L) or aCD3-CD28 coated beads (ratio 1bead:1cell).

The results show that NOD splenocytes respond to two peptides derived from the mIL-2 sequence by cell proliferation.

Conclusion

Since NOD mice present IL-2 specific T cells (reactive to two different peptides), the above results evidence that IL-2 specific T cells (detected by thymidine proliferation assay after re-stimulation with IL-2 peptides) could be used as a biomarker of T1D.

Example 11. Human IL-2 Neutralization Assay

PBMCs from healthy donors were cultured in 96-well plates in 75 µL/well in SVF-free RPMI medium (Gibco, France) containing 1 IU/mL of hIL-2 with or without heat-inactivated (30 min at 56° C.) serum (1/10 dilution) from hIL-2AAbs⁻ healthy donors or from ahIL-2AAbs⁺ T1D patients. After 5 min of stimulation, cultures were fixed with 225 µL/well of PBS/2% formaldehyde for 10 min at room temperature. After washing with PBS/0.2% BSA, cells were permeabilized with 100 µL/well of ice-cold methanol for 10 min on ice. Cells were then washed with PBS/0.2% BSA and stained with anti-CD3 PE-Cy7 (clone UCHT1; 1:200; Beckman-Coulter), anti-CD4 PerCP (clone RPA-T4 1:100; Ozyme), anti-CD25 PE (clone M-A251; 1:5; BD Biosciences and clone 3G10; 1:10; Miltenyi), anti-Foxp3 Alexa488 (clone 236A/E7; 1:20; eBiosciences) and anti-pSTAT5 Alexa647 (clone 47/Stat5(pY694); 1:20; BD Biosciences) for 45 min at 4° C. Cells were acquired on a LSRII or a Fortessa flow cytometer and analyzed with FlowJo software.

Figure 11:
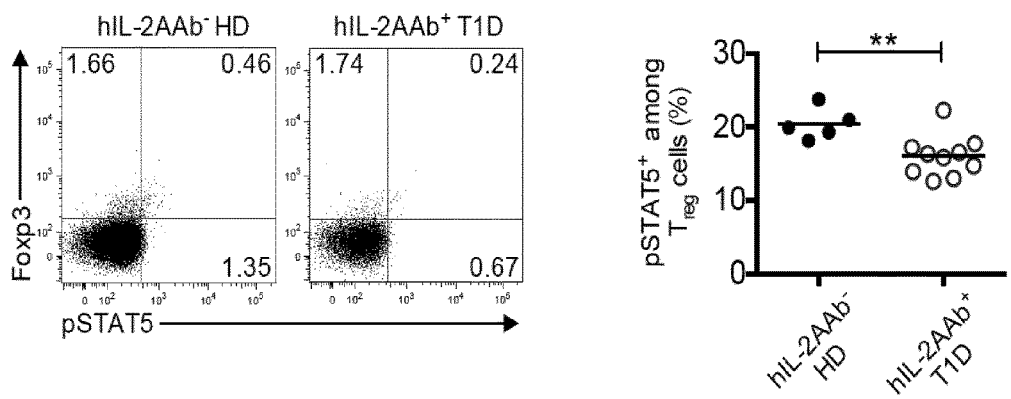
FIG. 11 shows the phosphorylation of STAT5 among regulatory T cells stimulated with IL-2 and pre-incubated with hIL-2AAb− HD serum or with hIL-2AAb+ T1D serum.

The results are shown in FIG. 11.

The graphs show that the percentage of pSTAT5 Tregs is decreased in presence of sera of patients containing anti-hIL-2 AutoAbs (right graph) but is not decreased in presence of sera of patients without anti-hIL-2 AutoAbs (left graph).

Conclusion

The above results evidence that the anti-IL-2 AutoAbs can have in vitro neutralizing activity.

Example 12. Vaccine

A vaccine preparation was manufactured from a water-in-oil emulsion constituted by 50% of ISA (SEPPIC, Paris) and 50% of an aqueous solution of the synthetic peptide LTRMLTFKFYMPKKA derived from human IL2 coupled with KLH (100 µg/dose).

---

The invention claimed is:

1. A peptide specifically recognized by anti-IL2 antibodies or IL-2-specific T cells of Type 1 diabetes (T1D), systemic lupus erythematosus, rheumatoid arthritis, Sjögren's syndrome and autoimmune polymyositis patients, wherein said peptide is derived from IL-2 and consists of amino acid sequence:

LTRMLTFKFYMPKKA, (SEQ ID No 1)

or

EFLNRWITFSQSIIS. (SEQ ID No 2)

2. A method of therapeutic treatment of a disease of the human or animal body, comprising a step of administering a peptide according to claim 1 to a subject in need thereof, wherein the disease of the human or animal body is selected from the group consisting of type 1 diabetes (T1D), systemic lupus erythematosus (SLE), rheumatoid arthritis (RA), Sjögren's syndrome (SJO) and autoimmune polymyositis (JO1).

3. The method according to claim 2, wherein the disease of the human or animal body is selected from the group consisting of type 1 diabetes (T1D), systemic lupus erythematosus (SLE), and rheumatoid arthritis (RA).

4. A pharmaceutical composition comprising as active ingredient a peptide according to claim 1 and a pharmaceutical excipient.

* * * * *